US00PP34862P2

(12) United States Plant Patent
Ulate

(10) Patent No.: US PP34,862 P2
(45) Date of Patent: Dec. 20, 2022

(54) ***DRACAENA* PLANT NAMED 'LIMÓN'**

(50) Latin Name: *Dracaena deremensis*
Varietal Denomination: LIMÓN

(71) Applicant: FLORICA FARMS, INC., Eustis, FL (US)

(72) Inventor: William Vasquez Ulate, Alajuela (CR)

(73) Assignee: FLORICA FARMS, INC., Eustis, FL (US)

( * ) Notice: Subject to any disclaimer, the term of this patent is extended or adjusted under 35 U.S.C. 154(b) by 0 days.

(21) Appl. No.: 17/687,291

(22) Filed: Mar. 4, 2022

(51) Int. Cl.
*A01H 5/02* (2018.01)
*A01H 6/12* (2018.01)

(52) U.S. Cl.
USPC ..... Plt./383
CPC ..... *A01H 6/12* (2018.05)

(58) Field of Classification Search
USPC ..... Plt./383
CPC ..... A01H 5/02
See application file for complete search history.

*Primary Examiner* — Kent L Bell
(74) *Attorney, Agent, or Firm* — Foley & Lardner LLP

(57) ABSTRACT

The variety 'LIMÓN' is a new and distinct cultivar of *Dracaena deremensis* plant. It can reach 75 cm height in a 21 cm diameter pot, with an average of approximately 34-40 leaves per plant. The arrangement of the leaves is base wrapped around the stem. Shows a dark green colored foliage, with marginal light green stripes.

3 Drawing Sheets

Latin name of the genus and species of the claimed plant: *Dracaena deremensis.*

Variety denomination: 'LIMÓN'.

BACKGROUND

The present invention relates to a new and distinct cultivar of *Dracaena* plant, botanically known as *Dracaena deremensis* of the family of Asparagaceae, hereinafter referred to by the cultivar name 'LIMÓN'.

*Dracaena* is a monocotyledonous and tropical foliage plant which can be produced as a single or multi-stemmed plant, used mainly as a house plant for interior use or outdoors in shades in zones 9 or 10 only.

The new *Dracaena* 'LIMÓN' originated as a naturally occurring whole plant mutation of *Dracaena deremensis* variety 'LEMON LIME' (unpatented). The new *Dracaena* 'LIMÓN' was discovered and selected by the inventor, William Vásquez Ulate, in 2020, as a single sprouting plant within a controlled environment, in Candelaria, Palmares, Alajuela province, Costa Rica.

'LIMÓN' was grown in tropical lowlands in Costa Rica with day lengths of 12 to 13 hours and ambient temperatures of 65 to 85 degrees Fahrenheit. The light levels in lux were 30 K and the level of relative humidity was 80%.

Asexual reproduction of the new *Dracaena* 'LIMÓN' by vegetative cuttings was first performed in 2020 in Candelaria, Palmares, Alajuela province, Costa Rica, and demonstrated that the combination of characteristics as herein disclosed for the new cultivar are firmly fixed and retained through successive generations of asexual reproduction.

SUMMARY

The following traits have been repeatedly observed and are determined to be unique characteristics of 'LIMÓN', which in combination distinguish this *Dracaena* as a new and distinct cultivar:

1. Dark green colored foliage, and light green color stripes in the margins of the leaf
2. Wide and lanceolate leaves, 40-45 cm long and supported in a rosette.
3. 0.5 m-0.75 m plant height in a 21 cm diameter pot.
4. Erect Plant habit.

Plants of the new *Dracaena* 'LIMÓN' differ from plants of the parental cultivar, *Dracaena deremensis* 'LEMON LIME' (unpatented) in the characteristics described in Table 1.

TABLE 1

Comparison between 'LIMÓN' and 'LEMON LIME'

| Characteristic | New Cultivar *Dracaena deremensis* 'LIMÓN' | Parent *Dracaena deremensis* 'LEMON LIME' (unpatented) |
|---|---|---|
| Plant Vigor | Less vigorous | More vigorous |
| Color | Dark green colored foliage, with smaller yellow stripes in leaf margins | Bright, glossy, yellow-green foliage which darkens to light-green as it matures and wider yellow tripes in leaf margins. |
| Shape | Lanceolate leaves on a rosette | Lanceolate leaves on a rosette |
| Texture of leaves | Smooth and waxy | Smooth and waxy |

Of the many commercial cultivars known to the present inventor, the most similar in comparison to the new *Dracaena deremensis* 'LIMÓN' is the commercial cultivar 'LEMON LIME' (unpatented).

BRIEF DESCRIPTION OF THE DRAWINGS

The accompanying photographs illustrate the overall appearance of the new *Dracaena deremensis* cultivar 'LIMÓN' showing the colors as true as is reasonably possible with colored reproductions of this type. Colors in the photographs may differ slightly from the color value cited in the detailed botanical descriptions which accurately describe the color of 'LIMÓN'.

DETAILED BOTANICAL DESCRIPTION

Figure 1:
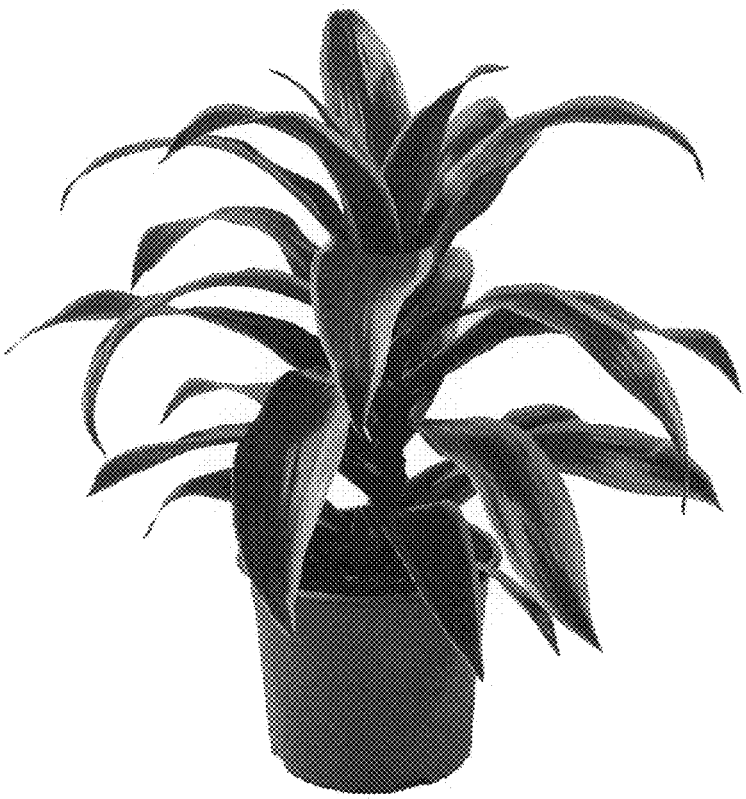
FIG. 1 shows a side view of a six-month old plant of *Dracaena* 'LIMÓN' in a 21 cm diameter pot.
Figure 2:
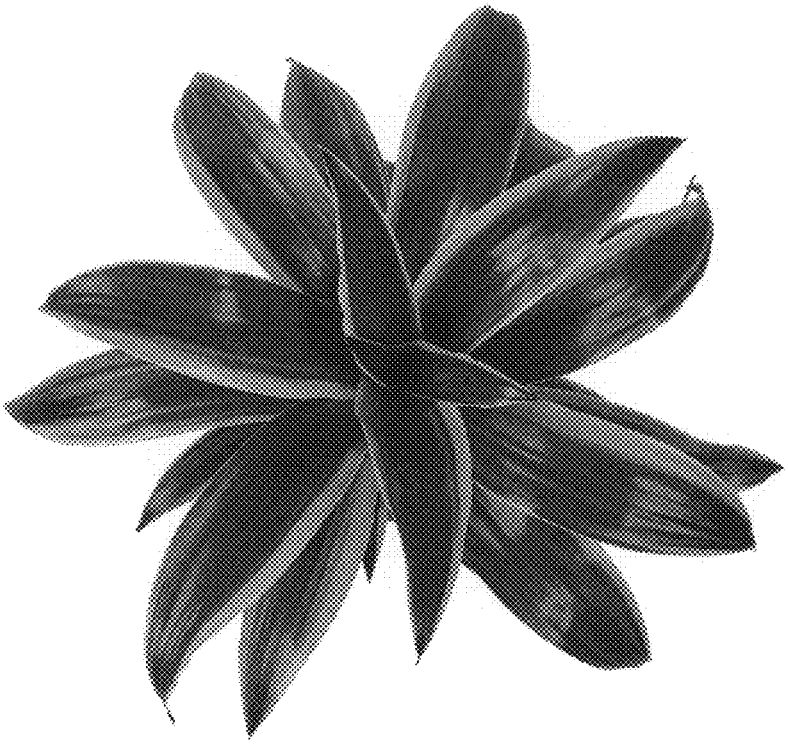
FIG. 2 shows a top view of a six-month old plant of *Dracaena* 'LIMÓN' in a 21 cm diameter pot.
Figure 3A:
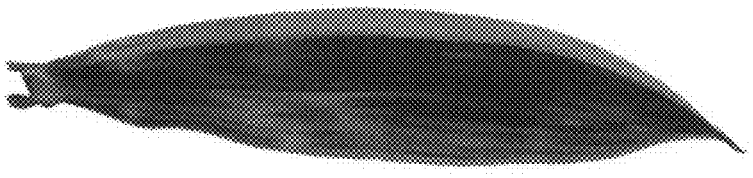
FIGS. 3A-3B show a close-up view of the typical leaves of *Dracaena* 'LIMÓN' from a six-month old plant (upper side 3A, under side 3B).
Figure 3B:
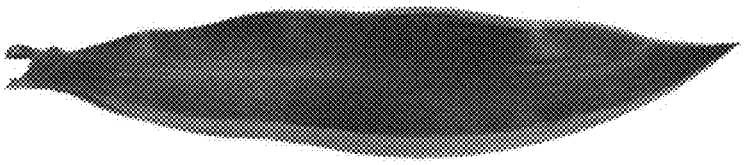

The new *Dracaena* 'LIMÓN' has not been observed under all possible environmental conditions. The phenotype of the new cultivar may show phenotypical changes with variations in environment such as temperature, light intensity, and day length without any change in the genotype of the plant.

The aforementioned photographs, together with the following observations, measurements and values describe the new *Dracaena* cultivar 'LIMÓN' as grown in open-field conditions at Baltimore, Matina, Limón province, Costa Rica, which closely approximate those generally used in commercial practice. Average temperature in Baltimore is 31° C. during the day and 24° C. at night. Plants grow under natural light conditions.

Plants of the new *Dracaena* cultivar 'LIMÓN' are grown under light conditions of about 80% shade from natural sunlight and about 80% relative humidity. No supplementary artificial light is necessary. Plants of the new *Dracaena* 'LIMÓN' are given 1) a liquid 24-8-16 fertilizer every 15 days, and 2) a granular Nutricote 18-6-12 fertilizer every 6 weeks in raining season. No growth retardants are used when growing plants of the new *Dracaena* 'LIMÓN'.

Color references were made according to The Royal Horticultural Society Colour Chart (RHS) online (rhscf.org-free.com). The photographs and descriptions were made during the dry season in Candelaria, Palmares, Alajuela province, Costa Rica when outdoor day average temperature was 31° C. The age of the plants described is 8 months old.

Classification:

*Botanical.*—*Dracaena deremensis.*

*Variety denomination.*—'LIMÓN'.

Parentage: Naturally occurring mutation of *Dracaena deremensis* 'LEMON LIME' (unpatented).

Optimal growth conditions:

*Light intensities.*—High adaptability to outdoor or indoor conditions.

*Temperature.*—Day: 18° C. to 28° C. Night: 14° C. to 22° C.

*Temperature tolerance.*—Tolerant to temperatures between 12° C. and 35° C.

*Fertilization.*—A liquid 24-8-16 fertilizer every 15 days, and a granular Nutricote 18-6-12 fertilizer every 6 weeks.

*Growth regulators.*—Not necessary.

Propagation:

*Type.*—Vegetative, by air layer cuttings.

*Rooting habit description.*—Easy to root. Roots are mostly fibrous and finely branched.

*Time to initiate roots.*—15 to 22 days at 20-25° C.

*Faster time to produce a rooted cutting.*—About 30 to 45 days at 20-25° C.

Plant:

*Growth rate.*—Approximately 77 cm annually.

*Form.*—Monocot; leaves whorled; leaf bases wrap around the stem.

*Plant height.*—Maximum of 1.50 m when grown in the ground and 0.5-0.75 m when grown in a container.

*Plant width.*—Single stem plant has an overall plant diameter of 56-76 cm wide.

*Stem-diameter.*—About 3.5 cm when grown in ground; about 1 cm when grown in 21 cm size container.

*Length.*—About 56-76 cm.

*Texture.*—Rough.

*Color.*—RHS N144D.

*Strength.*—Strong and durable.

*Internode length.*—About 20 mm to 40 mm.

Foliage:

*Quantity.*—About 34-40 leaves.

*Arrangement and attachment.*—Single, alternate; leaves whorled; leaf bases wrap around the stem.

*Leaf length.*—About 35-40 cm.

*Leaf width.*—About 6-8 cm.

*Overall shape of leaf.*—Lanceolated.

*Apex shape.*—Acute, triangular, and curved downwards.

*Base shape.*—Clasping to stem.

*Margin.*—Entire.

*Texture.*—Upper Surface: Smooth and waxy texture. Under Surface: Smooth and waxy texture.

*Pubescence.*—None.

*Color of mature leaf.*—Upper Surface: RHS N143B, and several RHS 144B complete and incomplete marginal stripes. Lower Surface: RHS N144C, and several RHS 144B complete and incomplete marginal stripes.

*Color of immature leaf.*—Upper Surface: RHS N143B central stripe, and several RHS 144B complete and incomplete marginal stripes. Lower Surface: RHS N144C central stripe, and several RHS 144B complete and incomplete marginal stripes.

*Central stripes average width.*—1.5-2.5 cm.

*Venation.*—Pattern: Longitudinal/parallel to the midrib. Color: RHS N143B.

*Leaf fragrance.*—None.

Inflorescence description: None observed.

Weather resistance: Drought tolerant.

Disease/pest resistance: None observed.

Disease/pest susceptibility: None observed.

I Claim:

1. A new and distinct *Dracaena* plant named 'LIMÓN', as described and illustrated herein.

* * * * *